US012731251B2

(12) United States Patent
Song et al.

(10) Patent No.: US 12,731,251 B2
(45) Date of Patent: Sep. 8, 2026

(54) MULTI ARM MACHINE LEARNING MODELS WITH ATTENTION FOR LESION SEGMENTATION

(71) Applicants: GENENTECH, INC., South San Francisco, CA (US); Hoffmann-La Roche Inc., Little Falls, NJ (US)

(72) Inventors: Zhuang Song, Albany, CA (US); Nils Gustav Thomas Bengtsson, South San Francisco, CA (US); Richard Alan Duray Carano, San Ramon, CA (US); David B. Clayton, Mountain View, CA (US); Alexander James Stephen Champion de Crespigny, Redwood City, CA (US); Laura Gaetano, Basel (CH); Anitha Priya Krishnan, Belmont, CA (US)

(73) Assignees: Genentech, Inc., South San Francisco, CA (US); Hoffmann-La Roche, Inc., Little Falls, NJ (US)

( * ) Notice: Subject to any disclaimer, the term of this patent is extended or adjusted under 35 U.S.C. 154(b) by 517 days.

(21) Appl. No.: 18/172,682

(22) Filed: Feb. 22, 2023

(65) Prior Publication Data

US 2023/0206438 A1 Jun. 29, 2023

Related U.S. Application Data

(63) Continuation of application No. PCT/US2021/047632, filed on Aug. 26, 2021.

(Continued)

(51) Int. Cl.

*G06K 9/00* (2022.01)
*G06T 7/00* (2017.01)

(Continued)

(52) U.S. Cl.

CPC .............. *G06T 7/0012* (2013.01); *G06T 7/11* (2017.01); *G06T 9/002* (2013.01); *G16H 30/40* (2018.01);

(Continued)

(58) Field of Classification Search

None

See application file for complete search history.

(56) References Cited

U.S. PATENT DOCUMENTS 11,372,066 B2 * 6/2022 Koch .................... G01R 33/16
2019/0049540 A1 2/2019 Odry et al.

(Continued)

OTHER PUBLICATIONS

Aslani et al., "Multi-Branch Convolutional Neural Network for Multiple Sclerosis Lesion Segmentation", Neuroimage, vol. 196, Apr. 3, 2019, pp. 1-15.

(Continued)

*Primary Examiner* — Wei Wen Yang

(74) *Attorney, Agent, or Firm* — Kilpatrick Townsend & Stockton LLP

(57) ABSTRACT

Embodiments disclosed herein generally relate to multi-arm machine learning models for lesion detection. Particularly, aspects of the present disclosure are directed to accessing a three-dimensional magnetic resonance imaging (MRI) images. Each of the three-dimensional MRI images depict a same volume of a brain of a subject. The volume of the brain includes at least part of one or more lesions. Each three-dimensional MRI image of the three-dimensional MRI images is processed using one or more corresponding encoder arms of a machine-learning model to generate an encoding of the three-dimensional MRI image. The encodings of the three-dimensional MRI images are concatenated to generate a concatenated representation. The concatenated representation is processed using a decoder arm of the machine-learning model to generate a prediction that iden- (Continued)

tifies one or more portions of the volume of the brain predicted to depict at least part of a lesion.

20 Claims, 8 Drawing Sheets

Related U.S. Application Data

(60) Provisional application No. 63/074,354, filed on Sep. 3, 2020.

(51) Int. Cl.
*G06T 7/11* (2017.01)
*G06T 9/00* (2006.01)
*G16H 30/40* (2018.01)
*G16H 50/20* (2018.01)

(52) U.S. Cl.
CPC ......... *G16H 50/20* (2018.01); *G06T 2200/04* (2013.01); *G06T 2207/10088* (2013.01); *G06T 2207/20021* (2013.01); *G06T 2207/20081* (2013.01); *G06T 2207/20084* (2013.01); *G06T 2207/30016* (2013.01); *G06T 2207/30096* (2013.01)

(56) References Cited

U.S. PATENT DOCUMENTS

2021/0267455 A1* 9/2021 Ghadimi .................. G06T 7/11
2022/0018922 A1* 1/2022 Shim ................. G01R 33/4625

OTHER PUBLICATIONS

International Application No. PCT/US2021/047632, "International Search Report and Written Opinion", mailed Nov. 5, 2021, 11 pages.
Zhang et al., "MS-GAN: GAN-based Semantic Segmentation of Multiple Sclerosis Lesions in Brain Magnetic Resonance Imaging", Digital Image Computing: Techniques and Applications (DICTA), IEEE, Dec. 10, 2018, pp. 1-8.
Hu et al., "Acu-Net: A 3D Attention Context U-Net for Multiple Sclerosis Lesion Segmentation", Institute of Electrical and Electronics Engineers, International Conference on Acoustics, Speech and Signal Processing, May 2020, pp. 1384-1388.
Xue, Y. et al.; "A multi-path decoder network for brain tumor segmentation"; New Jersey Institute of Technology (NJIT) website; 5th International MICCAI Brainlesion Workshop, BrainLes 2019, held in conjunction with the Medical Image Computing for Computer Assisted Intervention, MICCAI 2019, Shenzhen China; Oct. 17, 2019; 12 pages.

* cited by examiner

| Unet (threshold=0.5) | Average Dice | Average Dice (Total lesion load) < 5 ml | 5-15 ml | >= 15 ml | Precision (PPV) | Recall (sensi) | Absolute vol diff | Volume corr |
|---|---|---|---|---|---|---|---|---|
| 3D; 3 arm; single loss | 0.68 | 0.60 | 0.727 | 0.75 | 0.66 | 0.747 | 0.484 | 0.962 |
| 3D; 3 arm; Loss per depth | 0.681 | 0.612 | 0.724 | 0.743 | 0.63 | 0.791 | 0.576 | 0.951 |
| 3D; 3 arm; Loss per depth + att | 0.698 | 0.633 | 0.736 | 0.757 | 0.701 | 0.736 | 0.369 | 0.964 |

FIG. 5A

| Unet (overlap of 10%) | PPV | LTPR | LFPR |
|---|---|---|---|
| 3D; 3 arm; single loss | 0.851 | 0.815 | 0.215 |
| 3D; 3 arm; Loss per depth | 0.871 | 0.860 | 0.237 |
| 3D; 3 arm; Loss per depth + att | 0.892 | 0.821 | 0.182 |

FIG. 5B

| Unet (threshold=0.5) | Average Dice | Average Dice (Total lesion load) < 5 ml | 5-15 ml | >= 15 ml | Precision (PPV) | Recall (sensi) | Absolute vol diff | Volume corr |
|---|---|---|---|---|---|---|---|---|
| Stack Unet | 0.707 | 0.642 | 0.745 | 0.766 | 0.702 | 0.751 | 0.375 | 0.965 |
| 3D; Single arm | 0.694 | 0.624 | 0.738 | 0.757 | 0.67 | 0.764 | 0.432 | 0.957 |
| 3D; 3 arm; Loss per depth + att | 0.698 | 0.633 | 0.736 | 0.757 | 0.701 | 0.736 | 0.369 | 0.964 |

FIG. 6A

| Unet (overlap of 10%) | PPV | LTPR | LFPR |
|---|---|---|---|
| Stack Unet | 0.854 | 0.866 | 0.227 |
| 3D; single arm | 0.845 | 0.855 | 0.236 |
| 3D; 3 arm; Loss per depth + att | 0.892 | 0.821 | 0.182 |

FIG. 6B

| Method | Score | Dice coef | PPV | LTPR | LFPR | AVD |
|---|---|---|---|---|---|---|
| Top performing model | **93.39** | 0.6338 | 0.8694 | 0.4821 | 0.1347 | 0.3969 |
| Brungnara et al. (2020) | 93.03 | 0.681 | 0.855 | 0.538 | 0.157 | 0.366 |
| Multiarm Unet | 92.63 | 0.6779 | 0.8221 | 0.4751 | 0.1412 | 0.3366 |
| Hashemi et al. (2018) | 92.48 | 0.5841 | **0.9207** | 0.4135 | **0.0866** | 0.4972 |
| Aslani et al. (2019) | 92.12 | 0.6114 | 0.8992 | 0.4103 | 0.1393 | 0.4537 |
| Stack Unet | 91.61 | **0.6891** | 0.7861 | **0.5668** | 0.3414 | **0.3194** |
| Valverde et al. (2017) | 91.33 | 0.6304 | 0.7866 | 0.3669 | 0.1529 | 0.3384 |

FIG. 7

MULTI ARM MACHINE LEARNING MODELS WITH ATTENTION FOR LESION SEGMENTATION

CROSS-REFERENCE TO RELATED APPLICATIONS

This application is a continuation of International Application No. PCT/US2021/047632, filed on Aug. 26, 2021, which claims the benefit of and priority to U.S. Provisional Patent Application No. 63/074,354, filed on Sep. 3, 2020. Each of these applications is hereby incorporated by reference in its entireties for all purposes.

BACKGROUND

Multiple sclerosis (MS) is a disease that affects the central nervous system. Lesions form in the brains of subjects with MS as a result of the disease. The vast majority of the time, MS initially presents as relapsing-remitting MS, which is characterized by a separation in space and time. For example, a subject may experience multiple symptomatic episodes that are affecting different body areas and/or different functional systems. As another example, a subject may experience lesions in different parts of the central nervous system. As yet another example, a subject may experience a symptom and have a lesion in a brain area that does not correspond to the system. Over time, MS subjects' lesion size and count frequently increases, reflecting a worsening of the disease. Relapsing-remitting MS typically eventually progresses to secondary progressive MS, during which a gradual worsening of symptoms and brain health is observed rather than discrete symptomatic relapses and recovery episodes. Primary progressive MS similarly is characterized by the gradual symptom worsening and brain degradation, though this diagnosis is reserved for subjects who did not previously experience the relapsing-remitting form.

Magnetic resonance imaging (MRI) can provide visualization of new (contrast-enhanced) lesions, old lesions and brain atrophy (via brain-size changes). These metrics are bedrocks for supporting MS diagnoses, facilitating MS prognoses, selecting MS treatments and evaluating MS treatments. MRI images are generated using MRI sequences, which are particular settings of radio frequency pulses and gradients that result in a particular image appearance. Three prominent MRI sequence types include a T1 sequence, a T2 sequence, and a fluid-attenuated inversion recover (FLAIR) sequence.

T1 MRIs can be collected relatively quickly and provide structural information. Black holes-which are indicative of axonal destruction and neuron death-appear dark in T1 images. T2 MRIs are frequently used to show total disease burden. New and old lesions appear as hyperintense regions in these scans. FLAIR MRIs are similar to T2 MRIs, except that ventricles are darkened in FLAIR MRIs (while they are bright in T2 MRIs). Thus, lesions that appear near ventricles (e.g., in the corpus callosum) are more visible in FLAIR MRIs.

In some instances, a contrast agent (e.g., gadolinium) is administered to a subject (e.g., intravenously) before one or more MRI scans are collected to improve the visibility of active lesions. If the blood-brain barrier is intact, the contrast will not pass into the central nervous system. If the blood-brain barrier is disrupted, the contrast can traverse into the central nervous system and will localize in areas of inflammation. The contrast will appear as hyperintense in T1 MRIs.

Traditionally, a radiologist would manually annotate MRI scans. However, there are many scans to annotate, given that scans are collected for different depths and perspectives in addition to the difference in sequence types. Further, there is a high degree of variability in annotations across radiologists. Thus, it would be advantageous to identify an automated technique that can process MRI images, so as to improve efficiency and consistency.

SUMMARY

In some embodiments, a computer-implemented method is provided. A plurality of three-dimensional magnetic resonance imaging (MRI) images are accessed. Each of the plurality of three-dimensional MRI images depict a same volume of a brain of a subject. A first three-dimensional MRI image was generated using a first type of MRI sequence (e.g., T1, T2, or fluid-attenuated inversion recovery (FLAIR)) that is different than a second type of MRI sequence used to generate a second three-dimensional MRI image. Each three-dimensional MRI image of the plurality of three-dimensional MRI images is processed using one or more corresponding encoder arms of a machine-learning model to generate an encoding of the three-dimensional MRI image. The encodings of the plurality of three-dimensional MRI images are concatenated to generate a concatenated representation. The concatenated representation is processed using a decoder arm of the machine-learning model to generate a prediction that identifies one or more portions of the volume of the brain predicted to depict at least part of a lesion.

In some embodiments, the computer-implemented method further involves generating, for each three-dimensional MRI image of the plurality of three-dimensional MRI images, a downsampled encoding having a resolution that is lower than a resolution of the encoding of the three-dimensional MRI image. The downsampled encoding for each three-dimensional MRI image of the plurality of three-dimensional MRI images is processed using one or more layers of the one or more corresponding encoding arms. The downsampled encodings are concatenated to generate another concatenated representation. The prediction is further based on processing of the another concatenated representation using the decoder arm of the machine-learning model.

In some embodiments, the machine-learning model includes a U-Net machine-learning model.

In some embodiments, the machine-learning model includes one or more skip attention modules, each of the one or more skip attention modules connecting an encoding block of the encoding arms of the machine-learning model to a decoder block of the decoder arm at a same resolution.

In some embodiments, each skip attention module of the skip attention modules receives an input of the concatenated representation and an upsampled encoding of the another concatenated representation at the resolution of the three-dimensional MRI image. The prediction is further based on processing an output of skip-feature encodings from the skip attention modules using the decoder arm of the machine-learning model.

In some embodiments, the one or more skip attention modules include a residual connection between input and the output of the skip attention module to facilitate skipping the skip attention module if relevant high-dimensional features are unavailable.

In some embodiments, the machine-learning model was trained using a weighted binary cross entropy loss and/or a Tversky loss.

In some embodiments, the machine-learning model was trained using loss calculated at each of multiple depths of the machine-learning model.

In some embodiments, the first type of MRI sequence includes a sequence from a sequence set of T1, T2 and FLAIR, and the second type of MRI sequence includes another sequence from the sequence set.

In some embodiments, the computer-implemented method further involves determining a number of lesions using the prediction.

In some embodiments, the computer-implemented method further involves determining one or more lesion sizes or a lesion load using the prediction.

In some embodiments, the computer-implemented method further involves accessing data corresponding to a previous MRI. A change in a quantity, a size, or cumulative size of one or more lesions can be determined using the prediction and the data. An output is generated that represents the change.

In some embodiments, the computer-implemented method further involves recommending changing a treatment strategy based on the prediction.

In some embodiments, the computer-implemented method further involves providing an output corresponding to a possible or confirmed diagnosis of the subject of multiple sclerosis based at least in part on the prediction.

In some embodiments, the computer-implemented method further involves diagnosing the subject with multiple sclerosis based at least in part on the prediction.

Some embodiments of the present disclosure include a system including one or more data processors. The system can further include a non-transitory computer readable storage medium containing instructions which, when executed on the one or more data processors, cause the one or more data processors to perform part or all of one or more of the methods disclosed herein.

In some embodiments, a computer-program product is provided that is tangibly embodied in a non-transitory machine-readable storage medium. The computer-program product can include instructions configured to cause one or more data processors to perform part or all of one or more of the methods disclosed herein.

BRIEF DESCRIPTION OF THE DRAWINGS

FIGS. 5A-5B show exemplary results of multiple machine-learning models segmenting and detecting depictions of lesions in magnetic resonance imaging (MRI) images.

FIGS. 6A-6B show exemplary results of multiple machine-learning models segmenting and detecting depictions of lesions in MRI images.

FIG. 7 show exemplary results of detection of lesion depictions in MRI images using seven different machine-learning models.

DETAILED DESCRIPTION

I. Overview

Figure 1:
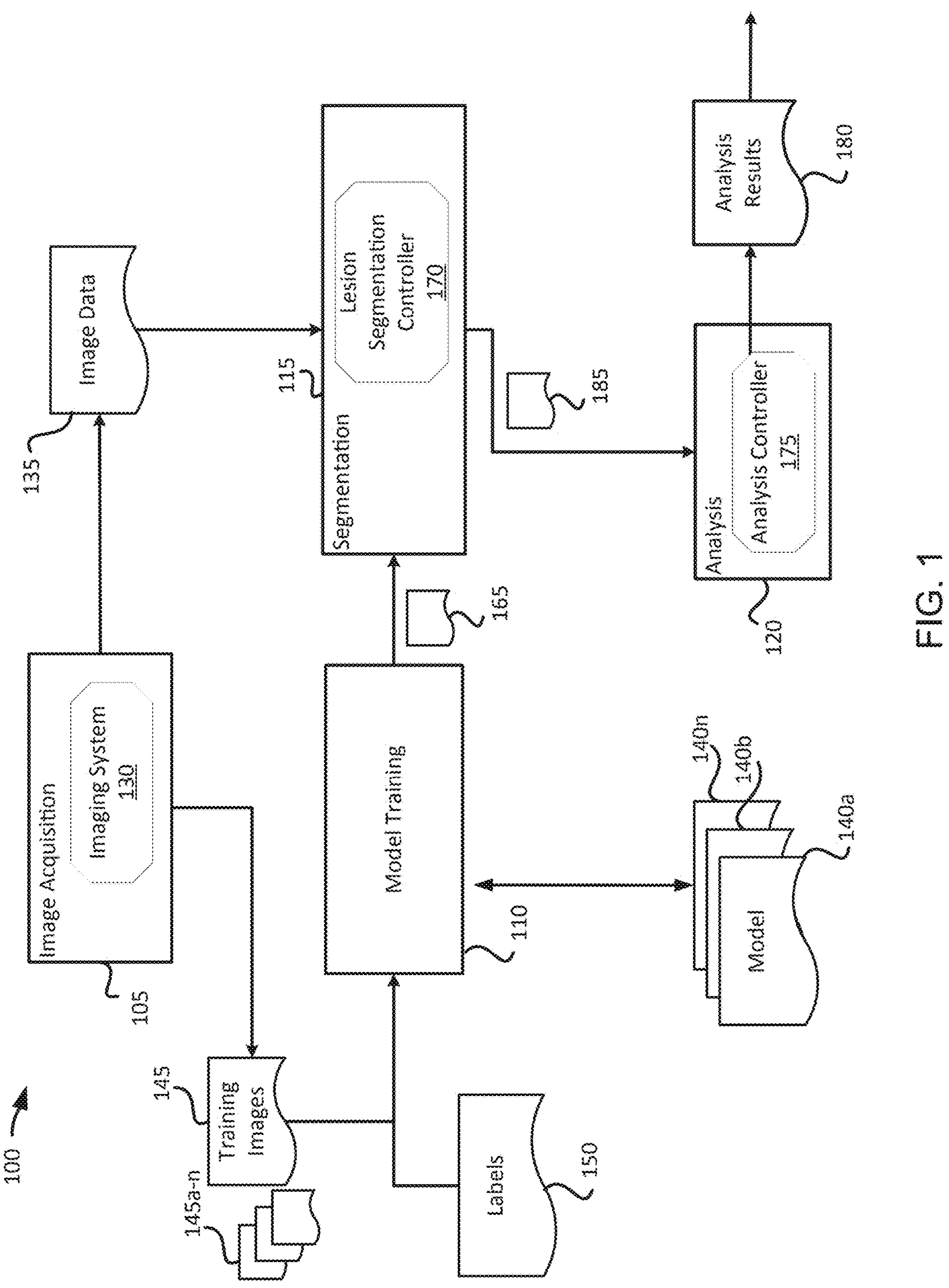
FIG. 1 illustrates an example computing environment for segmenting depictions of lesions within images using a model having multiple arms according to various embodiments.

The present disclosure describes techniques for automated lesion segmentation of medical images. More specifically, embodiments of the present disclosure provide techniques for segmenting depictions of lesions within medical images using trained multi-arm machine-learning networks. In some embodiments, machine-learning models with attention can be used to segment lesions in three-dimensional magnetic resonance imaging (MRI) images.

MRI images are typically annotated manually or semi-manually to identify lesions depicted in the MRI images. However, there are often many scans to annotate, given that scans are collected for different depths and perspectives in addition to the difference in sequence types (T1, T2, and fluid-attenuated inversion recovery (FLAIR)). Additionally, there is often a high degree of variability in annotations across annotators. Thus, manual or semi-manual approaches may result in suboptimal efficiency and consistency for lesion detection.

To address these limitations and problems, the techniques for automated object segmentation in some embodiments of the present disclosure utilize a multi-arm deep learning network trained for segmenting depictions of lesions. For example, a data processing system accesses multiple three-dimensional MRI images, each depicting a same volume of a brain of a subject. The volume of the brain includes at least part of one or more lesions. Each of the three-dimensional MRI images are generated using a different type of MRI sequence (e.g., T1, T2, or FLAIR). The data processing system processes each three-dimensional MRI image using one or more corresponding encoder arms of a machine-learning model to generate an encoding of the three-dimensional MRI images. Each encoder arm can be trained to process a different type of MRI sequence. The data processing system concatenates the encodings of the three-dimensional MRI images to generate a concatenated representation and processes the concatenated representation using a decoder arm of the machine-learning model to identify one or more portions of the volume of the brain predicted to depict at least part of a lesion. The lesion predictions may be output and further analyzed downstream. For example, the predicted lesion depictions may be used to predict whether a subject has any lesions, whether a subject has any enhancing lesions, how many lesions a subject has, how many enhancing lesions a subject has, a location (e.g., brain location) of each of one or more lesions, a location of each of one or more enhancing lesions, a size of each of one or more lesions that a subject has, a size of each of one or more enhancing lesions that a subject has, a cumulative lesion size for the subject, a cumulative enhancing lesion size for the subject, and/or a brain volume of the subject.

II. Techniques for Segmenting Medical Images

Image segmentation is a procedure to separate images into portions showing resemblance in different features like shape, size, color, etc. Segmentation of depictions of lesions allows visualization of the size and position of a lesion within a region of the body (e.g., the brain), and may also provide a basis for analysis of treatment. The gold standard of lesion segmentation has long been manual segmentation, which is time-consuming and labor-intensive, and thus unsuitable for large studies. Considerable research has been done to attempt to fully or partially automate the process of lesion segmentation. For example, image segmentation techniques such as thresholding, region growing, fuzzy clustering, use of the watershed algorithm, etc., have been used for separating depictions of abnormal tissues (e.g., lesions) from depictions of normal tissues, such as white matter (WM), gray matter (GM), and cerebrospinal fluid (CSF) of the brain. Nonetheless, the process of segmentation is still challenging due to the diversity of shape, location, and size of the depictions of lesions.

Described herein is an end-to-end method incorporating a model that uses multiple encoding arms of a machine-learning model (e.g., U-Net) to segment depictions of lesions. Treatment response may be characterized based on the segmented lesion depictions, along with other factors (e.g., relapse, progression, etc.). The developed model is devised to accommodate the complexity of three-dimensional scans, extreme imbalance between various lesion types, and the heterogeneous nature (e.g., variable density and object sizes) of the input images. As used herein, a "scan" is a graphical representation of signal on a single plane through the body of a subject. The model has comparable performance for lesion segmentation to conventional algorithms relying on manual intervention (e.g., manual selection of seeds or manual identification of bounding boxes), such as a thresholding method, an edge based segmentation method, or a region based segmentation method.

II.A. Example Computing Environment

FIG. 1 illustrates an example computing environment 100 (i.e., a data processing system) for segmenting depictions of lesions within images using a model having multiple arms according to various embodiments. As shown in FIG. 1, the segmenting performed by the computing environment 100 in this example includes several stages: an image acquisition stage 105, a model training stage 110, a segmentation stage 115, and an analysis stage 120.

The image acquisition stage 105 includes one or more imaging systems 130 (e.g., an MRI imaging system) for obtaining input images 135 (e.g., MRI images) of various parts of a subject. The imaging systems 130 are configured to use radiological imaging techniques such as MRI and the like to obtain the input images 135. The imaging systems 130 are able to determine the difference between various structures and functions within the subject based on characteristics (e.g., brightness, contrast, and spatial resolution) associated with each of the imaging systems 130 and generate a series of two-dimensional or three-dimensional images. Once the series of two-dimensional images are collected by the scanner's computer, the two-dimensional images can be digitally "stacked" together by computer analysis to reconstruct a three-dimensional image of the subject or a portion of the subject. The two-dimensional images and/or the reconstructed three-dimensional input images 135 allow for easier identification and location of basic structures (e.g., organs) as well as possible lesions or abnormalities. Each two-dimensional image and/or the reconstructed three-dimensional input image 135 may correspond to a session time and a subject and depict an interior region of the subject. Each two-dimensional image and/or the reconstructed three-dimensional input image 135 may further be of a standardized size, resolution, and/or magnification.

The model training stage 110 builds and trains one or more models 140*a*-140*n* (which may be referred to herein individually as a model 140 or collectively as the models 140) to be used by the other stages. The model 140 can be a machine-learning ("ML") model comprising multiple networks, such as a convolutional neural network ("CNN"), e.g. an inception neural network, a residual neural network ("Resnet"), a U-Net, a V-Net, a single shot multibox detector ("SSD") network, or a recurrent neural network ("RNN"), e.g., long short-term memory ("LSTM") models or gated recurrent units ("GRUs") models, or any combination thereof. The model 140 can also be any other suitable ML model trained in object detection and/or segmentation from images, such as a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). The computing environment 100 may employ the same type of model or different types of models for segmenting depictions of different type of lesions. The model 140 can include an encoder arm with a set of encoder models for generating features relevant for segmentation and detection of depictions of lesions and a decoder arm for generating lesion predictions 185. In certain instances, model 140 is constructed with a combined asymmetric loss function, e.g., a combination of Tversky loss and weighted binary cross entropy (wBCE) loss for training the network.

To train a model 140 in this example, training images 145 are generated by acquiring digital images, splitting the images into a subset of training images 145*a* for training (e.g., 90%) and a subset of training images 145*b* for validation (e.g., 10%), preprocessing the subset of training images 145*a* and the subset of training images 145*b*, augmenting the subset of training images 145*a*, and in some instances annotating the subset of training images 145*a* with labels 150. The subset of training images 145*a* are acquired from one or more imaging modalities (e.g., MRI T1, T2, proton density (PD), or FLAIR). In some instances, the subset of training images 145*a* are acquired from a data storage structure such as a database, an image system (e.g., one or more imaging systems 130), or the like associated with the one or more imaging modalities. Each image depicts one or more lesions.

The splitting may be performed randomly (e.g., a 90/10% or 70/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting. The preprocessing may comprise standardization or normalization to put all features on a same scale (e.g., a same size scale or a same color scale or color saturation scale). In certain instances, the images are resized with a minimum size (width or height) of predetermined pixels (e.g., 2500 pixels)

or with a maximum size (width or height) of predetermined pixels (e.g., 3000 pixels) and kept with the original aspect ratio. Augmentation can be used to artificially expand the size of the subset of training images 145*a* by creating modified versions of images in the datasets. Image data augmentation may be performed by creating transformed versions of images in the datasets that belong to the same class as the original image. Transforms include a range of operations from the field of image manipulation, such as shifts, flips, zooms, and the like. In some instances, the operations include random erasing, shifting, brightness, rotation, Gaussian blurring, and/or elastic transformation to ensure that the model 140 is able to perform under circumstances outside those available from the subset of training images 145*a*.

Annotation can be performed manually by one or more humans (annotators such as a radiologists or pathologists) confirming the presence of depictions of one or more lesions in each image of the subset of training images 145*a* and providing labels 150 to the one or more lesions, for example, drawing a bounding box (a ground truth) or segmentation boundary, using annotation software, around the area confirmed by the human to include the depictions of the one or more lesions. In certain instances, the bounding box or segmentation boundary may only be drawn for instances that have a greater than 50% in probability of being a lesion. For the images, which are annotated by multiple annotators, the bounding boxes or segmentation boundaries from all annotators may be used. In some instances, annotation data may further indicate a type of a lesion. For example, for various type of lesions, the annotation data may indicate the type, such as enhancing, non-enhancing, or T2 hyperintense lesions.

In some instances, a subset of training images 145 may be transmitted to an annotator device to be included within a training data set (i.e., the subset of training images 145*a*). Input may be provided (e.g., by a radiologist) to the annotator device using (for example) a mouse, track pad, stylus and/or keyboard that indicates (for example) whether the image depicts an object of interest (e.g., a lesion, an organ, etc.); a number and type of lesions depicted within the image; and a perimeter (bounding box or segmentation boundary) of each depicted lesion within the image. Annotator device may be configured to use the provided input to generate labels 150 for each image. For example, the labels 150 may include a number and/or type of lesions depicted within an image; a type classification for each depicted lesion; a number of each depicted lesion of a particular type; and a perimeter and/or mask of one or more identified lesions within an image. In some instances, labels 150 may further include a perimeter and/or mask of one or more identified lesions overlaid onto a medical image.

In some instances, the models 140 are trained and used to process a digital image of a three-dimensional (3D) patch of a brain. The 3D patch can be 96×96×32 and can include first portions that depict at least part of one or more lesions and second portions that each lack depiction of any lesions. The training data can include images generated using different MRI sequence types. For example, the training dataset can include three-dimensional MRI images generated using a T1 sequence, a T2 sequence, and a FLAIR sequence. The training data can include labels for portions depicting lesions and portions not depicting lesions. The labels may be received, identified or derived from data received from a database or a provider system. Label data can include (for example)—for a single image—an indication as to the portions of the image that depict at least part of a lesion, a quantity of lesions at least partly depicted in the image, locations within the image (e.g., particular voxels) that depict at least part of a lesion, a type of lesion (e.g., an enhancing lesion or non-enhancing lesion) at least partly depicted at a particular location within the image or within the image, etc.

Each of the set of encoder models of the model 140 can be trained to process a particular type of MRI sequence. For example, a first machine-learning model can be trained for MRI images of a T1 sequence; a second machine-learning model can be trained for MRI images of a T2 sequence; and a third machine-learning model can be trained for MRI images of a FLAIR sequence. Training data used to train the models 140 may include MRI images collected after a contrast agent was administered to a subject, MRI images that depict at least part of one or more contrast-enhanced lesions, MRI images collected without a contrast agent having been administered to a subject, MRI images collected before a contrast agent was administered to a subject, and/or MRI images that do not depict any contrast-enhanced lesions. For example, an encoder model of the model 140 may be trained only with images collected without a contrast agent having been recently administered to the subject, only with images collected after a contrast agent was recently administered to the subject, or with some of both types of images. It will be appreciated that an image collected after a contrast agent was administered may, in some instances, not depict any enhancing lesions in situations where the blood-brain barrier is intact and/or when a given scan does not depict a brain region to which contrast agent moved.

It will be appreciated that a machine-learning model technique disclosed herein may be trained and used to detect various types of lesions. For example, T2 lesions may be detected, enhancing T1 lesions may be detected, etc. In some instances, a machine-learning model technique disclosed herein may be trained and used to detect black holes.

In certain instances, the models 140 are trained using a weighted binary cross entropy (wBCE) loss or a Tversky loss. The loss function can capture multiple aspects such as region overlap, voxel-wise accuracy, surface mismatches, and possible penalties for false positives (FPs), false negatives (FNs), and AUC. The loss function may be a weighted binary cross entropy (wBCE, for quantifying voxel-wise accuracy) loss or a Tversky loss (e.g., for region overlap). Tversky loss may reduce false positives in the prediction 185 and wBCE may help identify smaller lesions. For example, the loss can be calculated using a Tversky loss with a beta of 0.7 to a weigh the contribution of false positives by 0.7 and to weigh the contribution of false negatives by 0.3. Additionally, a combination of Tversky loss and wBCE loss may be used to calculate the loss.

The training process for model 140 includes selecting hyperparameters for the model 140 and performing iterative operations of inputting images from the subset of training images 145*a* into the model 140 to find a set of model parameters (e.g., weights and/or biases) that minimizes a loss or error function for the model 140. The hyperparameters are settings that can be tuned or optimized to control the behavior of the model 140. Most models explicitly define hyperparameters that control different aspects of the models such as memory or cost of execution. However, additional hyperparameters may be defined to adapt a model to a specific scenario. For example, the hyperparameters may include the number of hidden units of a model, the learning rate of a model, the convolution kernel width, or the number of kernels for a model. Each iteration of training can involve finding a set of model parameters for the model 140 (configured with a defined set of hyperparameters) so that the value of the loss or error function using the set of model parameters is smaller than the value of the loss or error function using a different set of model parameters in a previous iteration. The loss or error function can be constructed to measure the difference between the outputs inferred using the models 140 and the ground truth segmentation boundary annotated to the images using the labels 150.

Once the set of model parameters are identified, the model 140 has been trained and can be validated using the subset of training images 145*b* (testing or validation data set). The validation process includes iterative operations of inputting images from the subset of training images 145*b* into the model 140 using a validation technique such as K-Fold Cross-Validation, Leave-one-out Cross-Validation, Leave-one-group-out Cross-Validation, Nested Cross-Validation, or the like to select the model with a minimum loss in the validation set over the epochs. The validation set can also be used to tune the hyperparameters and ultimately find the optimal set of hyperparameters. Once the optimal set of hyperparameters are obtained, a reserved test set of images from the subset of training images 145*b* are input into the model 140 to obtain output (in this example, the segmentation boundary around depictions of one or more lesions), and the output is evaluated versus ground truth segmentation boundaries using correlation techniques such as Bland-Altman method and the Spearman's rank correlation coefficients and calculating performance metrics such as the error, accuracy, precision, recall, receiver operating characteristic curve (ROC), etc.

As should be understood, other training/validation mechanisms are contemplated and may be implemented within the computing environment 100. For example, the model may be trained and hyperparameters may be tuned on images from the subset of training images 145*a* and the images from the subset of training images 145*b* may only be used for testing and evaluating performance of the model. Moreover, although the training mechanisms described herein focus on training a new model 140, these training mechanisms can also be utilized to fine tune existing models 140 trained from other datasets. For example, in some instances, a model 140 might have been pre-trained using images of other objects or biological structures or from sections from other subjects or studies (e.g., human trials or murine experiments). In those cases, the models 140 can be used for transfer learning and retrained/validated using the input images 135.

The model training stage 110 outputs trained models including one or more trained segmentation models 165 comprising a set of encoder arms and a decoder arm. One or more input images 135 are obtained by a lesion segmentation controller 170 within the segmentation stage 115. In various instances, the input images 135 are three-dimensional MRI images. Each of the three-dimensional MRI images depict a same volume of a brain of a subject. The volume of the brain includes at least part of one or more lesions. Each three-dimensional MRI image includes a three-dimensional patch of a full MRI image. The three-dimensional patch can be a subset of voxels of the full three-dimensional MRI image. In some instances, a first three-dimensional MRI image may be generated using a first type of MRI sequence that is different from a second type of MRI sequence used to generate a second three-dimensional MRI image. In certain instances, the three-dimensional MRI images obtained using different MRI sequences may be each input to a separate encoder arm of the segmentation models 165.

In some instances, the three-dimensional MRI images are preprocessed prior to being input into the segmentation models 165. For example, FLAIR MRI images can be intensity rescaled and z-scored. Additionally, to capture the increase in intensity of the lesions in T1 post-contrast images with respect to the T1 pre-contrast images, the volumes can be jointly normalized (e.g., rescaled maintaining the intensity relationship between the volumes). Both volumes can be z-scored using the mean and standard deviation of the brain in pre-contrast scans.

In some instances, the lesion segmentation controller 170 includes processes for processing three-dimensional MRI images using a trained segmentation model 165 comprising a set of encoder arms and a decoder arm. In some instances, each three-dimensional MRI image is input to a corresponding encoder arm of the trained segmentation model 165. Each encoder arm can generate an encoding of the three-dimensional MRI image. A downsampled encoding having a resolution that is lower than a resolution of the encoding of the three-dimensional MRI image can also be generated. The downsampled encoding can be processed using one or more layers of the one or more corresponding encoding arms. The encodings (or downsampled encodings) at a given resolution are aggregated (e.g., concatenated) to generate concatenated representations for each resolution. Each concatenated representation can be processed using a set of layers in the decoder arm of the segmentation model 165 to generate a prediction 185 that identifies one or more portions of the volume of the brain predicted to depict at least part of a lesion. The prediction 185 may identify a likelihood of each voxel including a depiction of a lesion. In some examples, the lesion segmentation controller 170 may output the prediction 185 an image that corresponds to the three-dimensional MRI image with estimated segmentation boundaries around depictions of the lesions.

In some instances, the segmentation model 165 may include skip features. Skip features are encoding features with fine details forwarded to the decoder arm. The decoder arm of the segmentation model 165 may receive an aggregation of skip-feature encodings as an output of a skip attention module, and generate the prediction 185 of depicted lesions based on using the skip-feature encodings. In some instances, the skip attention module can receive the concatenated representation at a given resolution and an upsampled encoding of another concatenated representation to the given resolution. The skip attention module can output a skip-feature encoding. The skip-feature encodings can be aggregated, which may involve a concatenation or summation of skip-feature encodings generated by a skip attention module of the segmentation model 165 at a given resolution and upsampled skip-feature encodings generated by upsampling results from skip attention modules at lower resolutions and/or downsampled skip-feature encodings generated by downsampling results from skip attention modules at higher resolutions. Alternatively, the decoder arm may receive skip-feature encodings from the skip attention modules at each resolution without aggregating upsampled or downsampled skip-feature encodings at other resolutions.

Though the skip features contain fine details, they may be noisy since skip features are generated by encoding layer with reduced receptive field (local region of the input image that the current convolution operation sees), and the skip features may lack context for correct classification of voxels, resulting in false positives (FPs). For example, blood vessels may look similar to small lesions when looking at a smaller portion of a scan, but when using high dimensional features learned from a larger portion of a scan it may become easier to learn the long and thin structure of blood vessels. In addition, the discrepancy at the edges or boundaries of structures in lower dimensional representations can be corrected using the semantic information learned from high dimensional representations. Hence, the skip attention module tries to reduce FPs by providing attention to areas in skip layers based on higher dimensional representation from the next level features with lower resolution.

The prediction 185 may be transmitted to an analysis controller 175 within the analysis stage 120. The analysis controller 175 includes processes for obtaining or receiving the prediction 185 for one or more of the resolutions and determining analysis results 180 based on the one or more predictions 185. The analysis controller 175 may further include processes for determining a number of lesions using the one or more predictions 185. The analysis controller 175 may further include processes for determining one or more lesion sizes or a lesion load using the one or more predictions 185. The number of lesions, the one or more lesion sizes, and/or the lesion load, may be output as the analysis results 180. The analysis controller 175 may further include processes for accessing data corresponding to a previous MRI, determining a change in a quantity, a size or cumulative size of one or more lesions using the prediction and the data, and generating the analysis results 180 as an output that represents the change. As an example, a care provider may recommend that a subject switch from a current treatment to another treatment based on a change (identified in the output) in a number of lesion depictions detected in recent MRI data as compared to older MRI data associated with the subject. The analysis controller 175 may further include processes for recommending changing a treatment strategy based on the prediction 185. The analysis controller 175 may further include processes for providing the analysis results 180 as an output corresponding to a possible or confirmed diagnosis of the subject of multiple sclerosis based at least in part on the prediction 185. For example, a care provider may identify a diagnosis (e.g., of a type of multiple sclerosis or of multiple sclerosis itself) based on a quantity of depictions of lesions detected and identified in the output. The analysis controller 175 may further comprise processes for diagnosing the subject with multiple sclerosis based at least in part on the prediction 185. The analysis controller 175 may further comprise processes for evaluating and/or predicting treatment response based at least in part on the prediction 185. For example, the analysis controller 175 can compare the prediction 185 to older MRI data for the subject to evaluate and/or predict treatment response. The diagnosis of multiple sclerosis, evaluation, and/or prediction of treatment response can be output as the analysis results 180.

In some embodiments, false positive predictions can be reduced using multiple techniques. The predictions can be masked with a white matter mask to reduce the false positives with a hypothesis that there is a differential distribution of true positives (TPs) and FPs in and outside the white matter (e.g., true T2 lesions are in white matter and false positives are outside the white matter). As MS lesions are caused by the immune system attacking myelin sheath around axons of neurons, it may be assumed that the TPs occur in the white matter. However, observing the differential distribution of FPs and TPs may be difficult. In such cases, a false positive term can also be added to the loss function to reduce the false positive predictions. Additionally, a smooth truncated loss can be implemented instead of wBCE to reduce learning from outliers. Additional machine-learning models (e.g., radiomics-based models) can also be implemented to classify predicted lesions into true positives and false positives.

While not explicitly shown, it will be appreciated that the computing environment 100 may further include a developer device associated with a developer. Communications from a developer device to components of the computing environment 100 may indicate what types of input images are to be used for the models, a number and type of models to be used, hyperparameters of each model, for example, learning rate and number of hidden layers, how data requests are to be formatted, which training data is to be used (e.g., and how to gain access to the training data) and which validation technique is to be used, and/or how the controller processes are to be configured.

II.B. Exemplary Models Comprising Multiple Encoder Arms

Figure 2:
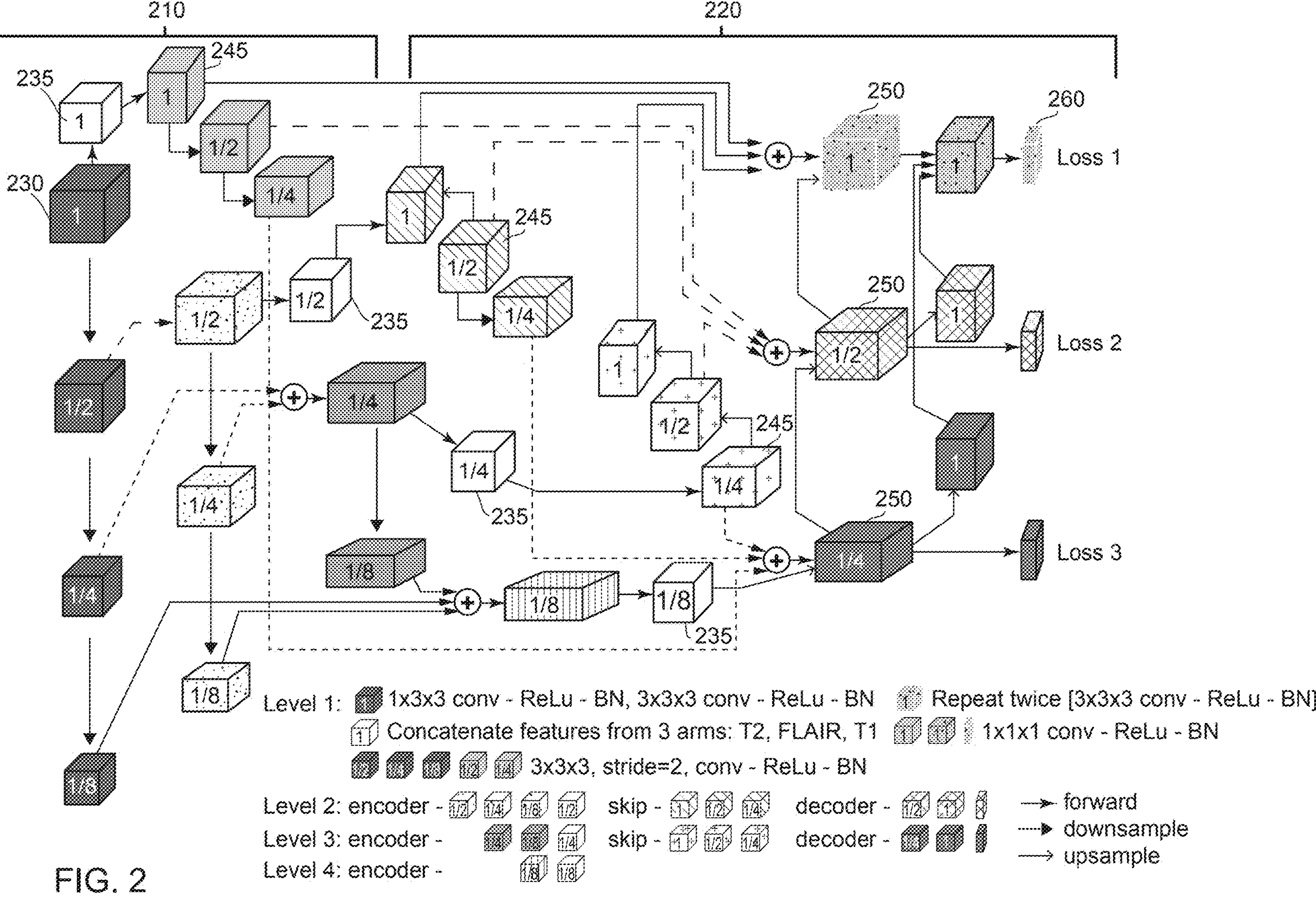
FIG. 2 shows an exemplary model comprising multiple encoder arms used to segment depictions of lesions according to various embodiments.

FIG. 2 shows an exemplary architecture that includes an encoder arm 210 used to generate encodings of MRI images and a decoder arm 220 used to transform the encodings into lesion predictions. The encoder arm 210 can include a set of models having a same architecture or having different architectures. The architecture corresponds to the segmentation model 165 in FIG. 1 that is used by the lesion segmentation controller 170 to determine lesion predictions.

In some instances, each of one, more or all encoder models of the encoder arm 210 can be configured to receive, as input, a three-dimensional MRI image, such as the input images 135 in FIG. 1. The three-dimensional MRI image may include a three-dimensional patch of a full MRI image. The three-dimensional patch can be a subset of voxels of the full three-dimensional MRI image. For example, an anisotropic voxel size of 1×1×3 $mm^3$ may be used to create a patch size of 96×96×32. Alternatively, an isotropic voxel size (e.g., 1×1×1 $mm^3$) and resulting patch size (96×96×96) can be used. Other patch sizes corresponding to anisotropic or isotropic voxel sizes are also usable. In some instances, the patch is a resampled (e.g., upsampled) patch.

In some instances, the set of encoder models of the encoder arm 210 includes multiple models configured to process input images and extract features at different scales. For example, the encoder arm 210 can include one or more models configured to process input images having dimensions of D (depth)×H (height)×W (width). Each arm can include multiple depth levels (e.g., four), with features extracted at each level (e.g., D×W×H, D/2×W/2×H/2, D/4×W/4×H/4 and D/8×W/8×H/8). The features extracted at lower depth levels can be downsampled encodings generated by downsampling the encodings at full resolution. The number of downsampled encodings corresponds to the number of down-sampling operations. A set of models of the encoder arm 210 can be used for encoding that are trained using different MRI sequence data. For example, the one or more models of the encoder arm 210 may include (for example) a first model trained using T1 MRI images, a second model trained using T2 MRI images, and a third model trained using FLAIR MRI images.

Encoding blocks 230 of the encoder arm 210 can include one or more sets of a convolution (e.g., 1×3×3 or 3×3×3) layer, a batch norm layer, and a rectified linear unit (ReLU) activation layer to generate an encoding of a respectively received input image (e.g., a three-dimension patch of an MRI image collected using a particular MRI sequence). Each of encoding blocks 230 can be configured to extract features from the input image. For example, for each level of the network, a set of feature arrays may be generated. The feature arrays may be downsampled using strided convolutions (e.g., 2×2×2).

For a given resolution, the encoding can be generated using an aggregation of downsampled encodings from higher depth levels. For example, at a depth level corresponding to ¼ resolution, the encoding block 230 can receive an aggregation of the feature representations from the higher depth levels (e.g., ½ resolution and the full resolution) that are downsampled to the ¼ resolution. The aggregation may involve summation or concatenation of the feature arrays. For instance, the feature representations may be summed to minimize computational requirements of the machine-learning model. With increased computational ability, the feature representations from each of the depth levels may be concatenated.

The feature representations from each encoder model for a given resolution can then be aggregated. For example, all feature arrays corresponding to all encoding arms across all input images having a given resolution (e.g., depth level) can be concatenated along a channel dimension while maintaining the feature shape at the given resolution. For example, for a given resolution, the feature array may include elements from multiple types of MRI sequences (e.g., T1, T2, FLAIR). Further, for each input data set (e.g., corresponding to a particular imaging session and particular subject), the encoder arm 210 generates multiple concatenated feature representations 235—each being associated with a particular resolution. Each of these concatenated feature representations 235 may itself include elements representing the multiple types of MRI sequences represented in the input data.

The concatenated representations 235 at each resolution can be processed using the decoder arm 220 (e.g., U-Net model). The decoder arm 220 can be trained using a loss function that quantifies the mismatch and/or discrepancy between the model predictions and ground truth masks. The loss may be output at each level (e.g., loss per depth), such that the machine-learning model learns representation at each level. The decoder arm 220 can process the concatenated representations 235 to generate the prediction 260 that identifies one or more portions of the volume of the brain depicting a part of a lesion (e.g., a part of a non-enhancing lesion, a part of an enhancing lesion or a part of any type of lesion).

In some instances, the decoder arm 220 can include one or more skip attention modules 245. Skip attention modules 245 connect two non-adjacent layers of the machine-learning model in order to forward fine-grained details extracted by encoding blocks 230 of the encoder arm 210, to be combined with semantic features from upsampling blocks of the decoder arm 220. Decoder blocks 250 of the decoder arm 220 can receive skip-feature encodings generated by the skip attention modules 245 to generate a prediction 260 of lesions depicted in the three-dimensional MRI image. At each resolution, the decoder block 250 can receive an aggregation of skip-feature encodings generated at multiple resolutions. For example, at the full resolution level, the skip attention module 245, which includes one or more sets of a convolution (e.g., 1×1×1) layer, a ReLU activation layer, and a batch norm layer, can process the concatenated representation 235. The skip-feature encoding generated by the skip attention module 245, along with other skip-feature encodings generated by upsampling outputs of the other skip attention modules 245 to the full resolution are aggregated. For lower resolutions, the skip-feature encodings of the skip attention module at the given resolution can be aggregated with upsampled skip-feature encodings generated by upsampling results of the skip attention modules 245 at resolutions lower than the given resolution to the given resolution. Additionally, the aggregation can include downsampled skip-feature encodings generated by downsampling results of the skip attention modules 245 at higher resolutions than the given resolution. For the aggregation, feature representations from the same encoder model may be summed, and feature representations from different encoder models may be concatenated.

The decoder blocks 250 of the machine-learning model can output a prediction 260, which is an example of the prediction 185 in FIG. 1. For example, the prediction 260 can identify one or more portions of the volumes of the brain predicted to depict at least part of a lesion. The prediction 260 may be used in determining a number of lesions, lesion sizes, or a lesion load in the volume of the brain. The prediction 260 may further be used in combination with data corresponding to a previous MRI to determine a change in a quantity, size, or cumulative size of the lesions. Additionally, a recommendation for changing a treatment strategy can be determined based on the prediction 260. In some instances, the prediction 260 may also be used to diagnose the subject with multiple sclerosis.

Figure 3:
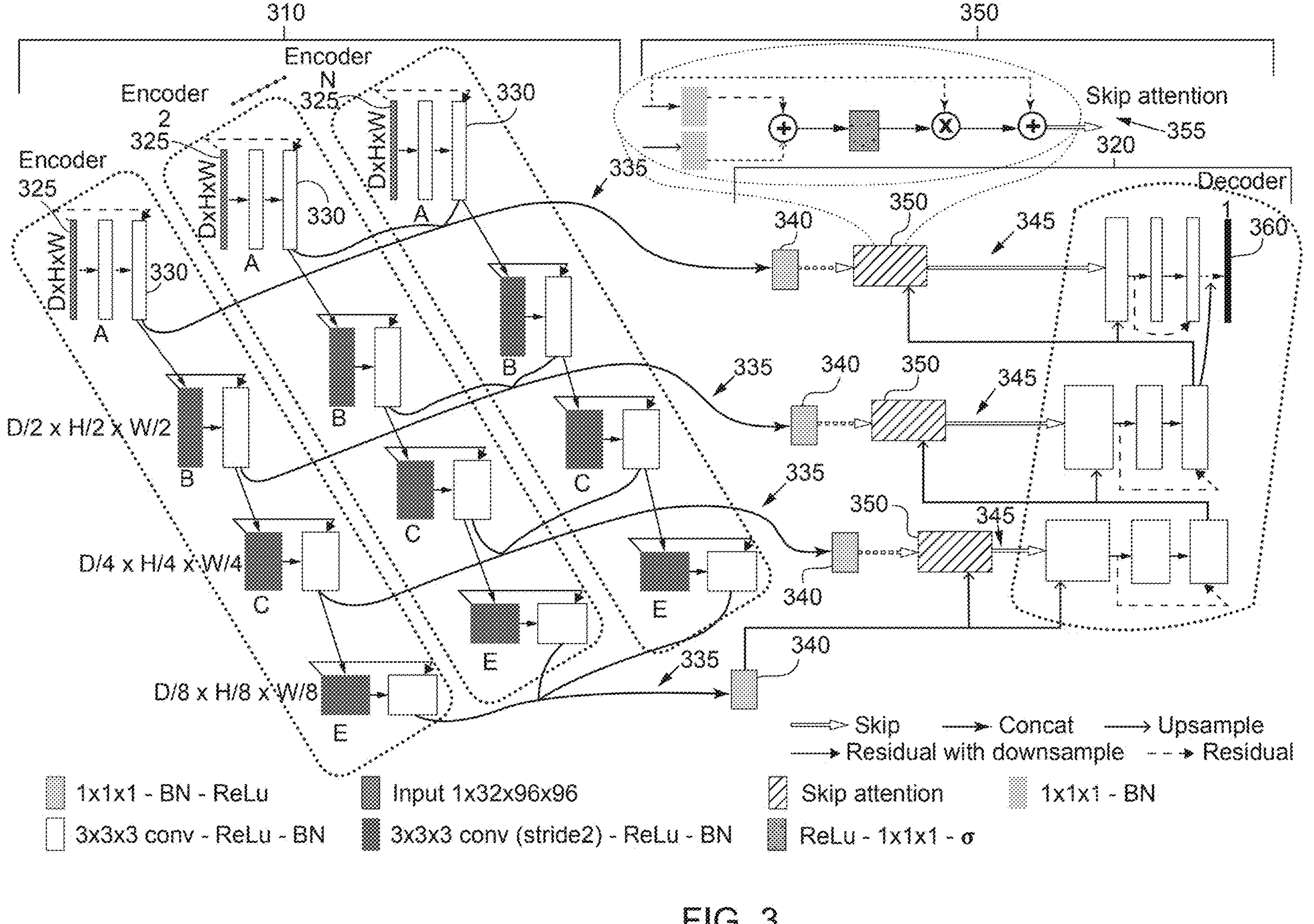
FIG. 3 shows another exemplary model comprising multiple encoder arms used to segment depictions of lesions according to various embodiments.

FIG. 3 shows another exemplary architecture that includes an encoder arm 310 with a set of encoder models used to generate encodings of MRI images and a decoder arm 320 used to transform the encodings into lesion predictions. The set of encoder models can include a set of models having a same architecture or having different architectures. The architecture corresponds to the segmentation model 165 in FIG. 1 that is used by the lesion segmentation controller 170 to determine lesion predictions.

In some instances, each of one, more or all encoder models of the encoder arm 310 can be configured to receive, as input, a three-dimensional MRI image (e.g., input images 135 in FIG. 1). The three-dimensional MRI image may include a three-dimensional patch of a full MRI image. The three-dimensional patch can be a subset of voxels of the full three-dimensional MRI image. For example, an anisotropic voxel size of 1×1×3 $mm^3$ may be used to create a patch size of 96×96×32. Alternatively, an isotropic voxel size (e.g., 1×1×1 $mm^3$) and resulting patch size (96×96×96) can be used. Other patch sizes corresponding to anisotropic or isotropic voxel sizes are also usable. In some instances, the patch is a resampled (e.g., upsampled) patch.

In some instances, the set of encoder models of the encoder arm 310 includes multiple models configured to process input images 325 (e.g., input images 135 in FIG. 1) and extract features at different scales. For example, the encoder arm 310 can include one or more models configured to process input images 325 having dimensions of D (depth)×H (height)×W (width). Each arm can include multiple depth levels (e.g., four), with features extracted at each level (e.g., D×W×H, D/2×W/2×H/2, D/4×W/4×H/4 and D/8×W/8×H/8). The features extracted at lower depth levels can be downsampled encodings generated by downsampling the encodings at full resolutions. The number of downsampled encodings corresponds to the number of downsampling operations. A set of models of the encoder arm 310 can be used for encoding that are trained using different MRI sequence data. For example, the one or more models of the encoder arm 310 may include (for example) a first model trained using T1 MRI images, a second model trained using T2 MRI images and a third model trained using FLAIR MRI images.

Encoding blocks 330 of the encoder arm 310 can include one or more sets of a convolution (e.g., 3×3×3) layer, a batch norm layer, and a ReLU activation layer to generate an encoding of a respectively received input image 325 (e.g., a three-dimension patch of an MRI image collected using a particular MRI sequence). Each of encoding blocks 330 can be configured to extract features from the input image 325. For example, for each level of the network, a set of feature arrays may be generated. The feature arrays may be down sampled using strided convolutions (e.g., 2×2×2).

For a given resolution, the encodings can be aggregated. For example, all feature arrays corresponding to all encoding arms across all input images having a given resolution (e.g., depth level) can be concatenated 335 along a channel dimension while maintaining the feature shape at the given resolution. For example, for a given resolution, the feature array may include elements from multiple types of MRI sequences (e.g., T1, T2, FLAIR). Further, for each input data set (e.g., corresponding to a particular imaging session and particular subject), the encoder arm 310 generates multiple concatenated feature representations 340—each being associated with a particular resolution. Each of these concatenated feature representations 340 may itself include elements representing the multiple types of MRI sequences represented in the input data.

The concatenated representations 340 at each resolution can be processed using the decoder arm 320 (e.g., U-Net model). The decoder arm 320 can be trained using a loss function that quantifies the mismatch and/or discrepancy between the model predictions and ground truth masks. The loss may be output at each level (e.g., loss per depth), such that the machine-learning model learns representation at each level. The decoder arm 320 can process the concatenated representations 340 to generate the prediction that identifies one or more portions of the volume of the brain depicting a part of a lesion (e.g., a part of a non-enhancing lesion, a part of an enhancing lesion or a part of any type of lesion).

In some instances, the decoder arm 320 can include one or more skip attention connections 345. Skip attention connections 345 connect two non-adjacent layers of the machine-learning model in order to forward fine-grained details extracted by encoding blocks 330 of the encoder arm 310, to be combined with semantic features from upsampling blocks of the decoder arm 320. Skip features have a lower receptive field (local region of the input image that the current convolution operation sees), and the skip features may lack context for correct classification of voxels, resulting in FPs. For example, blood vessels may look similar to small lesions when looking at a smaller context, but when using high dimensional features learned from a larger context it becomes easier to learn the long and thin structure of blood vessels. In addition, the discrepancy at the edges or boundaries of structures in lower dimensional representations can be corrected using the semantic information learned from high dimensional representations. The machine-learning model can further include skip attention modules 350 that receive the concatenated representations 340 to propagate features through skip connections 345 in order to emphasize and/or modulate fine features from the encoding blocks 330 of the encoder arm 310 by coarse features from a higher level representation, such as one level deeper on the decoder arm 320. The skip attention modules 350 can reduce FPs introduced by the skip features, which can result in an improved prediction of lesion depictions. The skip attention modules 350 use soft attention, which can be learned with standard back-propagation techniques. In one embodiment, the skip attention modules 350 include at least one hidden layer connected to a non-adjacent layer and/or adjacent prior layer via a residual connection 355. The residual connection 355 between the hidden layer and an adjacent prior layer or a non-adjacent layer may be used to bypass the path where skip features are multiplied by voxel-wise attention learned from the sum of skip features and upsampled features. The residual connection 355 bypasses the attention based on determining the upsampled features include an insufficient signal. MS lesions tend to be small, so there might not be enough signal in the high dimensional features to guide the skip features. Hence, the residual connection 355 bypasses the attention from high dimensional features if needed.

The machine-learning model can output the prediction 360, which can be an example of the prediction 185. The prediction 360 can identify one or more portions of the volumes of the brain predicted to depict at least part of a lesion. The prediction 360 may be used in determining a number of lesions, lesion sizes, or a lesion load in the volume of the brain. The prediction 360 may further be used in combination with data corresponding to a previous MRI to determine a change in a quantity, size, or cumulative size of the lesions. Additionally, a recommendation for changing a treatment strategy can be determined based on the prediction 360. In some instances, the prediction 360 may also be used to diagnose the subject with multiple sclerosis.

II.C. Exemplary Process

Figure 4:
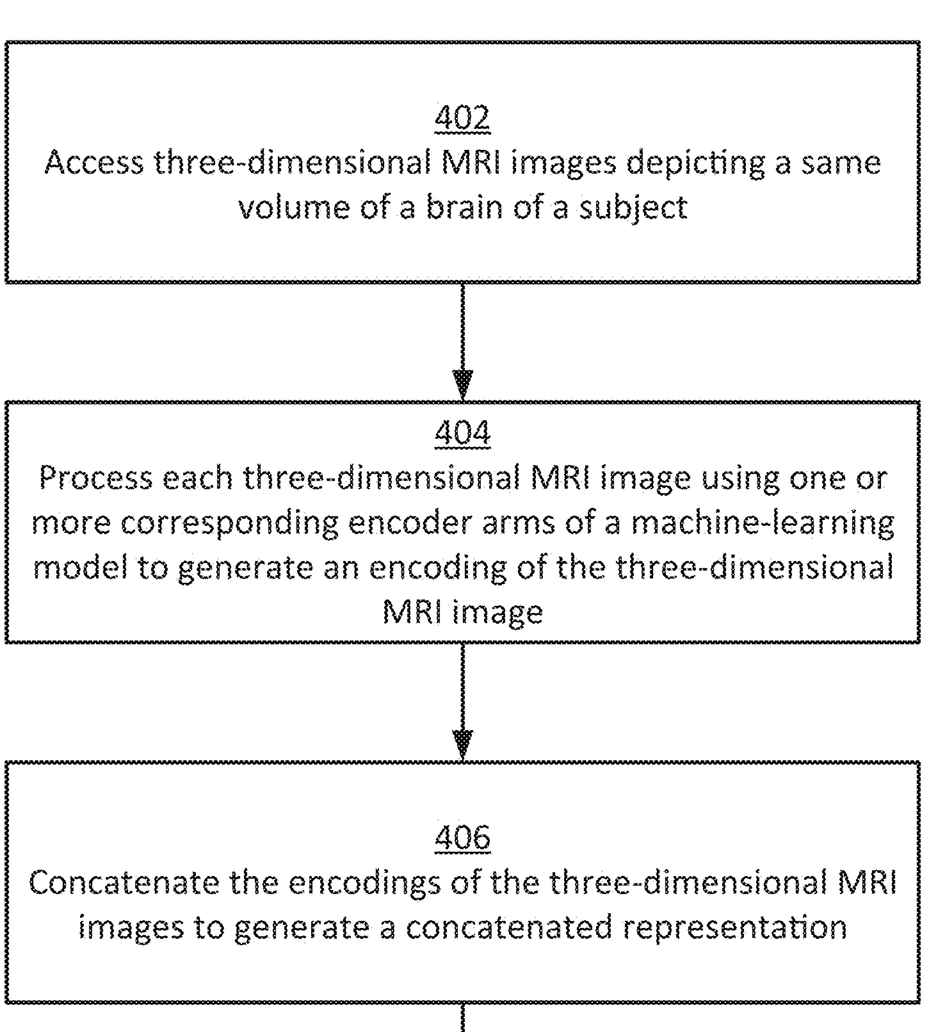
FIG. 4 illustrates an exemplary process for segmenting depictions of lesions within images using a model having multiple encoder arms according to various embodiments.

FIG. 4 illustrates an exemplary process for segmenting depictions of lesions within images using a model having multiple encoder arms according to various embodiments. At block 402, three-dimensional MRI images (e.g., input images 135 in FIG. 1) are accessed. The three-dimensional MRI images depict a same volume of a brain of a subject. The volume of the brain includes at least part of one or more lesions. Additionally, a first three-dimensional MRI image of the three-dimensional MRI images can be generated using a first type of MRI sequence (e.g., T1, T2, or FLAIR) that is different than a second type of MRI sequence used to generate a second three-dimensional MRI image of the three-dimensional MRI images. The three-dimensional MRI images can be accessed by a segmentation controller (e.g., lesion segmentation controller 170) from an imaging system (e.g., imaging system 130).

At block 404, each three-dimensional MRI image of the three-dimensional MRI images is processed using one or more corresponding encoder arms of a machine-learning model (e.g., segmentation model 165 in FIG. 1). Each encoder arm of the machine-learning model can correspond to a type of MRI sequence, so three-dimensional MRI images generated by a particular type of MRI sequence can be processed by the encoder arm that corresponds to the particular type of MRI sequence. The encoder arms can generate an encoding of each of the three-dimensional MRI images.

At block 406, the encodings of the three-dimensional MRI images are concatenated to generate a concatenated representation (e.g., concatenated representations 235 or concatenated representations 340). The encodings from each encoder arm (e.g., corresponding to a particular type of MRI sequence) can be concatenated. The concatenation can be performed at each resolution, such that there can be a concatenated representation generated for each resolution.

At block 408, the concatenated representation is processed using a decoder arm of the machine-learning model to generate a prediction that identifies one or more portions of the volume of the brain predicted to depict at least part of a lesion. The prediction may then be output. A number of lesions, one or more lesions sizes, and/or a lesion load can be determined using the prediction. Data corresponding to a previous MRI may be accessed, a change in a quantity, a size or cumulative size of one or more lesions using the prediction and the data may be determined, and an output that represents the change may be generated. A change may be recommended for a treatment strategy based on the prediction. Additionally or alternatively, an output corresponding to a possible or confirmed diagnosis of the subject of multiple sclerosis based at least in part on the prediction may be provided. The subject may be diagnosed with multiple sclerosis based at least in part on the prediction.

III. Examples

III.A. Example I

To evaluate model performance, data sets were collected from Opera I (NCT01247324) and tested on Opera II (NCT01412333) datasets (baseline, 24, 48 and 96 weeks). Each data set included MRI images and an indication as to which voxels within the MRI images depicted lesions (enhancing, non-enhancing, or T2 hyperintense). Various model architectures were trained using the opera1 data set and tested on the independent opera2 data set to generate performance results.

Each of the model architectures used an encoder arm 310 with a set of encoder models. The encoder arm 310 included a first model configured to receive T1-weighted images, a second model configured to receive T2-weighted images and a third model configured to receive FLAIR images. Each of the set of encoder models included multiple depth levels for extracting features of the images. Each of the first set of encoder models was configured to output multiple feature arrays. For each depth level, the feature arrays generated by all of the corresponding models were concatenated. The concatenated arrays were fed to a decoder arm 320.

The subsequent model may include:

- A stack U-net model configured to receive an encoding generated in a single arm (by one encoding model) of a concatenation of three consecutive T1 slices (of 256×256×3 voxels), three consecutive T2 slices and three consecutive FLAIR slices as input using a single loss or loss per depth (Stack Unet):
- A U-net model configured to receive an encoding generated in a single arm (by one encoding model) of a concatenation of a T1 patch (of 96×96×32 voxels), T2 patches and FLAIR patches as input using a single loss ("3D; Single loss");
- A U-net model configured to receive encodings generated in three arms (by three encoding models) corresponding to three types of images (T1, T2 and FLAIR) trained using a single loss ("3D; 3 arm; single loss");
- A U-net model configured to receive encodings generated in three arms corresponding to three types of images (T1, T2 and FLAIR) trained using losses calculated at each of multiple depths ("3D; 3 arm; loss per depth"); and
- A U-net model with skip attention connections configured to receive encodings generated in three arms corresponding to three types of images (T1, T2 and FLAIR) trained using losses calculated at each of multiple depths ("3D; 3 arm; loss per depth+att").

For each model, the images were treated cross-sectionally (e.g., ignoring the time and longitudinal information). Model predictions were evaluated for segmentation (per voxel) and detection (per lesion) performance. In a subsequent longitudinal analysis, new and enlarging lesions were identified from serial lesion masks using a heuristic approach.

The 3D; 3 arm; loss per depth+att model has the architecture shown in FIG. 3. Specifically, the model included an encoder arm 310 (e.g., a multi-arm encoder) to extract features separately from 3D T1-weighted MRI image patches, 3D T2-weighted MRI image patches and 3D FLAIR image patches. The encoder arms were designed to have the same receptive fields in all dimensions. Anisotropic kernels were used to handle anisotropic image resolution (using a voxel size of 1×1×3 $mm^3$) for Opera 1 and 2 data sets (NCT01247324 and NCT01412333, respectively), to reduce memory and computation requirements relative to training and running the model using an unsampled 1×1×1 $mm^3$ resolution. A patch size of 96×96×32 was used for the Opera data sets. For the ISBI data set, isotropic kernels were used, as the preprocessed images were resampled to have 1×1×1 $mm^3$ resolution.

The 3D; 3 arm; loss per depth+att model was a U-Net model configured to include nodes located across a U-shaped distribution of levels that extend from a highest level to a lowest level (i.e., bridge level) back to the highest level, with outputs from each level being fed to the next (lower or higher level). The decoder arm 320 included skip attention modules 350 such that gating signals are provided from one level deeper or higher. The skip attention modules 350 included residual connections 355 that can be used to bypass the attention from high-dimensional features, if appropriate.

A combination of Tversky loss and weighted binary cross entropy loss were used to train the U-net machine-learning model. The weighted binary cross entropy loss is a voxel-wise loss and was used to help segment smaller lesions. To account for large imbalance between the foreground/lesion class and background, weighted binary cross entropy weighs the foreground heavily (in response to a corresponding hyperparameter setting). Adding weighted binary cross entropy helped detect smaller lesions but also risked generating increased false positives. To reduce false positives, Tversky loss was also used. The beta variable was set to 0.7, such that the contribution from false positives was 0.7 and from false negatives was 0.3. Deep supervision with loss at every level was used to promote network learning representations at each level.

FIG. 5A shows results comparing performance of the 3D; 3 arm; single loss model with the 3D; 3 arm; loss per depth model to understand the effect of deep supervision and with the 3D; 3 arm; loss per depth+att model to understand the effect of attention. The segmentation results were calculated by characterizing accuracy of predictions at a voxel level. Notably, the average dice score (defined to be twice the true positives divided by the sum of the false negatives, false positives and two times the true positives) was higher for the model that included attention connections as compared to the other models that did not, and the dice scores for the model that used loss per depth were higher than those from the single-loss model. This result held true regardless as to whether the dice score was calculated across all images, images associated with a <5 ml lesion load, 5-15 ml lesion load or 15 ml or higher lesion load. Further, the attention model achieved superior precision (defined as the number of true positives divided by the sum of true positives and false positives) and superior absolute volume difference (AVD, defined as the absolute difference in predicted and GT volumes divided by GT volume). While the sensitivity decreased by ~1%, there was substantial improvement in precision and AVD for the attention model.

FIG. 5B shows results of detection using the three different machine-learning models. The detection results were calculated by characterizing accuracy of predictions at a lesion level. Statistics calculated included lesion positive predicted values (PPV, defined as the true positive number of lesions divided by the sum of true positives and false positives), lesion-wise true positive rate (LTPR) and lesion-wise false positive rate (LFPR, defined as the false positive number of lesions divided by the sum of predicted true positives and false positives). The model that included the attention connections achieved the highest PPV and lowest LFPR values relative to the other models that were evaluated. The 3D; 3 arm; loss per depth model also achieved a higher PPV score relative to the single-loss model. These results suggest that both loss per depth and skip attention modules (e.g., skip attention modules 245 and skip attention modules 350) improve the ability to segment and detect lesions.

FIG. 6A shows results of segmentation using three different machine-learning models using 2.5D and 3D input MRI images. Two-dimensional and three-dimensional models are commonly used in lesion detection. Stack Unet is a slight improvement from 2D and captures local context. Since a majority of MS lesions are small, the stack Unet would have best sensitivity. Patch Unet is a simple anisotropic 3D network, which captures more context. The patch Unet and variants of the patch Unet were the best performing models for the ISBI dataset. A multi-arm patch model was used based on the observation in GT masks that in some cases the lesion information could be present in one of the input channels and not in others.

With regard to segmentation (voxel-level-performance), the Stack Unet and the multi-arm Unet were comparable, with the Stack Unet achieving the highest dice scores and precision. However, as shown in FIG. 6B, the Stack Unet had more false positives relative to the three-arm model. Thus, with regard to detection (lesion-level performance), the Stack Unet achieved the higher performance with regard to LTPR. The 3D; arm; loss per depth+att model had increased LPPV and lower LFPR but at the expense of LTPR.

FIG. 7 shows results of segmentation and detection using seven different machine-learning models. The models were evaluated on the ISBI dataset. Performance metrics included scores (combination of the other metrics), dice coefficients, PPV, LTPR, LTFR, and AVD.

The multi-arm Unet model achieved comparable dice coefficients, LTPR, and AVD to top performing models. These results suggest the multi-arm Unet model, as described in FIGS. 2 and 3, is able to accurately detect lesion voxels and lesion counts.

III.B. Example 2

Lesions are frequently evaluated during clinical studies to predict whether a given therapeutic is effective at treating multiple sclerosis so as to slow progression of the disease. In particular, study endpoints frequently examine an extent to which a lesion count and/or lesion size (e.g., cumulative lesion size) changed during a study period. The change observed when a particular treatment was administered during the study period can be compared to a corresponding change observed when no treatment or a baseline treatment was administered during the study period.

Data for this example compares the change in new and enlarging T2 lesion counts when ocrelizumab 400 mg was administered as compared to interferon-beta-1α 44 μg. The lesion masks from serial MRI scans were used in a longitudinal analysis to develop a heuristic approach to identify and estimate the number of new and enlarging T2 lesions at weeks 24, 48 and 96 with respect to the preceding timepoint (baseline, w24 and w48, respectively). The heuristics were tuned on GT lesion masks to match the percent decrease of mean number of new and enlarging T2 lesions between treatment (Ocr) arms and control (Inf) arms. The heuristic approach was applied to T2 lesion segmentation masks from the three models described previously (Stack Unet, Patch Unet, and multi-arm Unet) along with two ground truth models (automated and automated with a minimum lesion size of three voxels). The percent decrease in this imaging endpoint between treatment and control arms was estimated at weeks 24, 48 and 96. In order to understand if there was a significant difference in this endpoint across arms, a negative binomial regression of the number of new and enlarging T2 lesions was performed with treatment arm, presence of T1 Gd-enhancing lesions at baseline (yes or no), baseline expanded disability status score (EDSS, <4 vs >=4) and geographic region (USA vs rest of world) as independent variables.

Results were calculated for each of:

Ground truth: Original analysis of the Opera datasets by radiologists. Two manual radiologist reads were performed on the MRI images. The first read was for lesion segmentation at every time point (e.g., baseline, w24, w48, w96). The second read was for detecting new and enlarging T2 lesions given earlier segmentations and candidate new/enlarging lesions.

Automated GT: Automation of new/enhancing T2 lesion detection given GT radiologist reads at baseline, w24, w48 and w96 without the second read from radiologists. For example, lesion segmentations at baseline and w24 were used to determine what lesions were new at w24. This process was done for each successive pairs (e.g., w24 and w48, w48 and w96).

Automated GT (GT>=three voxels): Lesion detection using the automated GT approach while enforcing a minimum lesion size of 3 voxels.

Stack: A stack U-net model was configured to receive an encoding generated in a single arm (by one encoding model) of a concatenation of three consecutive T1 slices (of 256×256×3 voxels), three consecutive T2 slices and three consecutive FLAIR slices as input using a single loss. Lesion detection using the automated approach for identifying new and enlarging T2 lesions applied to the T2 lesions predicted by the stack U-net model ("2.5D; Single loss").

Patch: A U-net model was configured to receive an encoding generated in a single arm (by one encoding model) of a concatenation of a T1 patch (of 96×96×32 voxels), T2 patches and FLAIR patches as input using a single loss. Lesion detection using the automated approach for identifying new and enlarging T2 lesions applied to the T2 lesions predicted by the patch U-net model ("3D; Single loss").

Multi-arm Unet: A U-net model with skip attention connections configured to receive encodings generated in three arms corresponding to three types of images (T1, T2 and FLAIR) trained using losses calculated at each of multiple depths. Lesion detection using the automated approach for identifying new and enlarging T2 lesions applied to the T2 lesions predicted by the multi-arm U-net model with skip attention connections ("3D; 3 arm; loss per depth+att"). This is the embodiment of FIG. 3 as discussed in the prior example.

Figure 8:
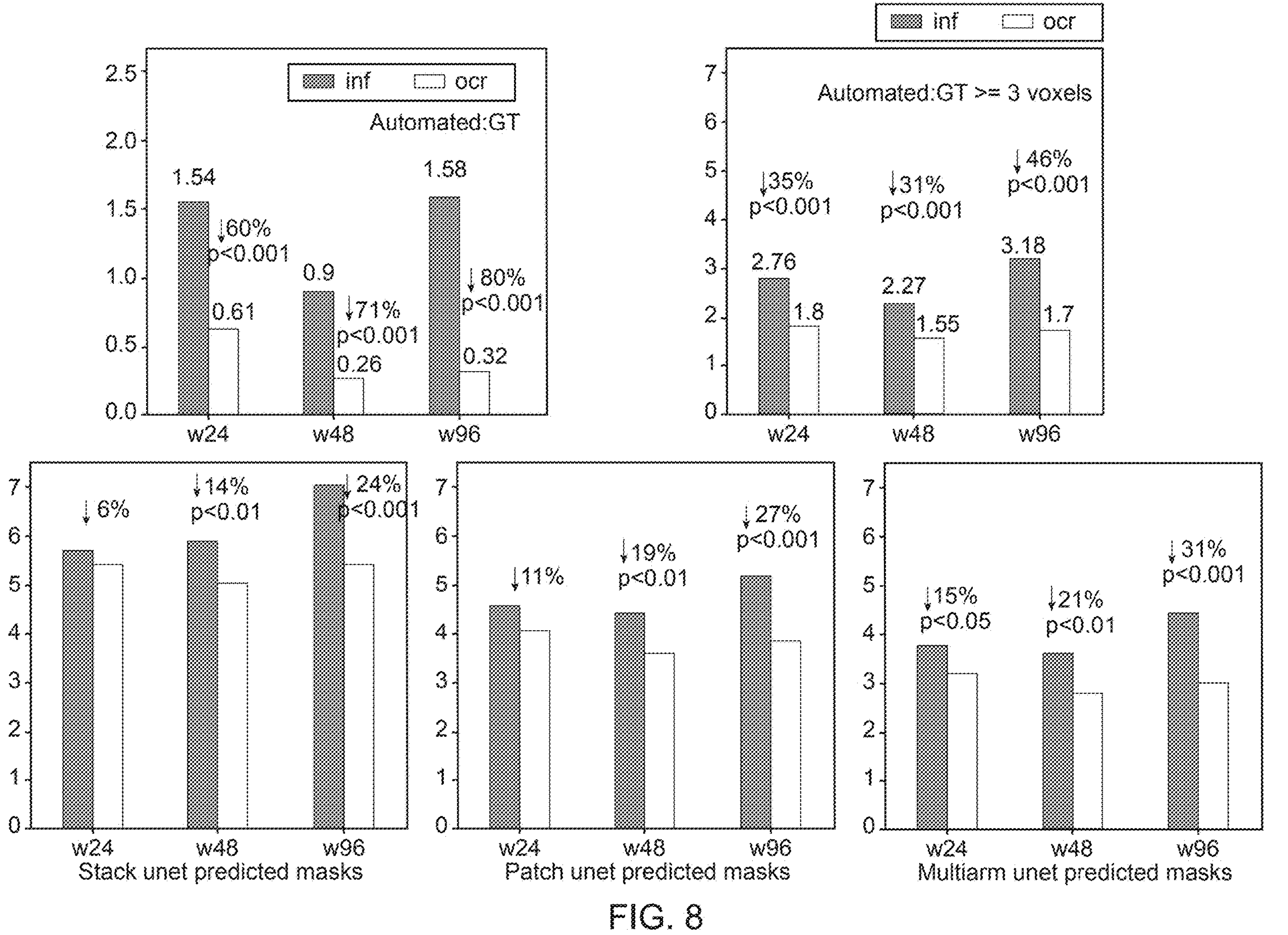
FIG. 8 shows exemplary results of lesion count prediction during clinical treatment using different machine-learning models.

As shown in FIG. 8, the clinical data showed that T2 lesion counts were significantly different between the two treatment groups at each of the three time points. According to manual radiologist reads, at weeks 24, 48, and 96 the subject group that received interferon-beta-1α (Inf) had an average of ~1.8, ~1.0, and ~2.5 new/enlarging T2 lesions, respectively. The subject group that received Ocrelizumab (Ocr) had an average of ~0.7, ~0.1, and ~0.1 new/enlarging T2 lesions at weeks 24, 48, and 96, respectively. The subject group that received Ocr had 61%, 96%, and 97% fewer new/enlarging T2 lesions at weeks 24, 48, and 96, respectively, than the subject group that received Inf. The percent reductions between the subject groups differed significantly (p-values of <0.001) for each timepoint. The automated GT approach and the automated GT (GT>=three voxels) approach successfully predicted the significant difference at each time point, though these techniques relied upon manual lesion segmentation annotations at each time point.

All three fully automated techniques (stack, patch and multi-arm Unet) captured the significant difference between the treatment groups at the 48-week and 96-week time points. However, the multi-arm Unet technique, as detailed in both FIGS. 2 and 3, was the only fully automated technique for which MRI-image processing outputs successfully captured the significant difference between the treatment groups at the 24-week time point.

Further, the average lesion counts generated by the multi-arm Unet technique were closer to those from the clinical database. The other two fully automated techniques, meanwhile, resulted in average lesion counts that overshot the true average lesion counts more substantially, indicating that these other techniques had more false positives as compared to the multi-arm Unet technique of FIGS. 2 and 3. Also, the percent reduction from all three models were significantly lower than that from manual assessment, indicating the inadequacy of the heuristic approach to identify new/enlarging T2 lesions.

IV. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

V. Example Embodiments

As used below, any reference to a series of examples is to be understood as a reference to each of those examples disjunctively (e.g., "Examples 1-4" is to be understood as "Examples 1, 2, 3, or 4").

Example 1 is a computer-implemented method comprising: accessing a plurality of three-dimensional magnetic resonance imaging (MRI) images, wherein each of the plurality of three-dimensional MRI images depict a same volume of a brain of a subject; and a first three-dimensional MRI image was generated using a first type of MRI sequence that is different than a second type of MRI sequence used to generate a second three-dimensional MRI image; processing, for each three-dimensional MRI image of the plurality of three-dimensional MRI images, the three-dimensional MRI image using one or more corresponding encoder arms of a machine-learning model to generate an encoding of the three-dimensional MRI image; concatenating the encodings of the plurality of three dimensional MRI images to generate a concatenated representation; and processing the concatenated representation using a decoder arm of the machine-learning model to generate a prediction that identifies one or more portions of the volume of the brain predicted to depict at least part of a lesion.

Example 2 is the computer-implemented method of example 1, further comprising: generating, for each three-dimensional MRI image of the plurality of three-dimensional MRI images, a downsampled encoding having a resolution that is lower than a resolution of the encoding of the three-dimensional MRI image; processing, for each three-dimensional MRI image of the plurality of three-dimensional MRI images, the downsampled encoding using one or more layers of the one or more corresponding encoding arms; and concatenating the downsampled encodings to generate another concatenated representation, wherein the prediction is further based on processing of the another concatenated representation using the decoder arm of the machine-learning model.

Example 3 is the computer-implemented method of example(s) 1-2, wherein the machine learning model includes a U-Net machine-learning model.

Example 4 is the computer-implemented method of any of example(s) 1-3, wherein the machine-learning model includes one or more skip attention modules, each of the one or more skip attention modules connecting an encoding block of the encoding arms of the machine-learning model to a decoder block of the decoder arm at a same resolution.

Example 5 is the computer-implemented method of example(s) 1-4, wherein each skip attention module of the skip attention modules receives an input of the concatenated representation and an upsampled encoding of the another concatenated representation at the resolution of the three-dimensional MRI image, and wherein the prediction is further based on processing an output of skip-feature encodings from the skip attention modules using the decoder arm of the machine-learning model.

Example 6 is the computer-implemented method of example(s) 1-5, wherein the one or more skip attention modules include a residual connection between the input and the output of the skip attention module to facilitate skipping the skip attention module if relevant high-dimensional features are unavailable.

Example 7 is the computer-implemented method of any of example(s)s 1-6, wherein the machine learning model was trained using a weighted binary cross entropy loss and/or a Tversky loss.

Example 8 is the computer-implemented method of any of example(s)s 1-7, wherein the machine learning model was trained using loss calculated at each of multiple depths of the machine-learning model.

Example 9 is the computer-implemented method of any of example(s)s 1-8, wherein the first type of MRI sequence includes a sequence from a sequence set of T1, T2 and fluid-attenuated inversion recovery (FLAIR), and the second type of MRI sequence includes another sequence from the sequence set.

Example 10 is the computer-implemented method of any of example(s)s 1-9, further comprising: determining a number of lesions using the prediction.

Example 11 is the computer-implemented method of any of example(s)s 1-10, further comprising: determining one or more lesion sizes or a lesion load using the prediction.

Example 12 is the computer-implemented method of any of example(s)s 1-11, further comprising: accessing data corresponding to a previous MRI; determining a change in a quantity, a size or cumulative size of one or more lesions using the prediction and the data; and generating an output that represents the change.

Example 13 is the computer-implemented method of any of example(s)s 1-12, further comprising: recommending changing a treatment strategy based on the prediction.

Example 14 is the method of any of example(s)s 1-13, further comprising: providing an output corresponding to a possible or confirmed diagnosis of the subject of multiple sclerosis based at least in part on the prediction.

Example 15 is the method of any of example(s)s 1-14, further comprising: diagnosing the subject with multiple sclerosis based at least in part on the prediction.

Example 16 is a system comprising: one or more data processors; and a non-transitory computer readable storage medium containing instructions which, when executed on the one or more data processors, cause the one or more data processors to perform part or all of one or more methods disclosed herein.

Example 17 is a computer-program product tangibly embodied in a non-transitory machine-readable storage medium, including instructions configured to cause one or more data processors to perform part or all of one or more methods disclosed herein.

What is claimed:

1. A computer-implemented method comprising:

accessing a plurality of three-dimensional magnetic resonance imaging (MRI) images, wherein each of the plurality of three-dimensional MRI images depicts a same volume of a brain of a subject; and a first three-dimensional MRI image was generated using a first type of MRI sequence that is different from a second type of MRI sequence used to generate a second three-dimensional MRI image;

processing, for each three-dimensional MRI image of the plurality of three-dimensional MRI images, the three-dimensional MRI image using one or more corresponding encoder arms of a machine-learning model to generate an encoding of the three-dimensional MRI image, wherein the one or more corresponding encoder arms comprise a plurality of encoder models, wherein the plurality of encoder models comprises a first encoder model trained for the first type of MRI sequence and a second encoder model trained for the second type of MRI sequence, and wherein the first three-dimensional MRI image is processed by the first encoder model and the second three-dimensional MRI image is processed by the second encoder model;

concatenating the encodings of the plurality of three-dimensional MRI images to generate a concatenated representation; and processing the concatenated representation using a decoder arm of the machine-learning model to generate a prediction that identifies one or more portions of the volume of the brain predicted to depict at least part of a lesion.

2. The computer-implemented method of claim 1, further comprising:

generating, for each three-dimensional MRI image of the plurality of three-dimensional MRI images using the corresponding encoder model, a downsampled encoding having a resolution that is lower than a resolution of the encoding of the three-dimensional MRI image;

processing, for each three-dimensional MRI image of the plurality of three-dimensional MRI images, the downsampled encoding using one or more layers of the one or more corresponding encoder arms; and concatenating the downsampled encodings to generate another concatenated representation, wherein the prediction is further based on processing of the another concatenated representation using the decoder arm of the machine-learning model.

3. The computer-implemented method of claim 2, wherein the machine-learning model includes one or more skip attention modules, each of the one or more skip attention modules connecting an encoding block of the one or more corresponding encoder arms of the machine-learning model to a decoder block of the decoder arm at a same resolution.

4. The computer-implemented method of claim 3, wherein each skip attention module of the one or more skip attention modules receives an input of the concatenated representation and an upsampled encoding of the another concatenated representation at the resolution of the three-dimensional MRI image, and wherein the prediction is further based on processing an output of skip-feature encodings from the skip attention modules using the decoder arm of the machine-learning model.

5. The computer-implemented method of claim 4, wherein the one or more skip attention modules include a residual connection between the input and the output of the skip attention module to facilitate skipping the skip attention module if relevant high-dimensional features are unavailable.

6. The computer-implemented method of claim 1, wherein the machine-learning model was trained using a weighted binary cross entropy loss and/or a Tversky loss.

7. The computer-implemented method of claim 1, wherein the machine-learning model was trained using loss calculated at each of multiple depths of the machine-learning model.

8. The computer-implemented method of claim 1, wherein the first type of MRI sequence includes a sequence from a sequence set of T1, T2 and fluid-attenuated inversion recovery (FLAIR), and the second type of MRI sequence includes another sequence from the sequence set.

9. The computer-implemented method of claim 1, further comprising:

determining a number of lesions using the prediction.

10. The computer-implemented method of claim 1, further comprising:

determining one or more lesion sizes or a lesion load using the prediction.

11. The computer-implemented method of claim 1, further comprising:

accessing data corresponding to a previous MRI;

determining a change in a quantity, a size or cumulative size of one or more lesions using the prediction and the data; and generating an output that represents the change.

12. The computer-implemented method of claim 1, further comprising:

recommending changing a treatment strategy based on the prediction.

13. The computer-implemented method of claim 1, further comprising:

providing an output corresponding to a possible or confirmed diagnosis of the subject of multiple sclerosis based at least in part on the prediction.

14. A system comprising:

one or more data processors; and a non-transitory computer readable storage medium containing instructions which, when executed on the one or more data processors, cause the one or more data processors to perform a set of actions including:

accessing a plurality of three-dimensional magnetic resonance imaging (MRI) images, wherein each of the plurality of three-dimensional MRI images depicts a same volume of a brain of a subject; and a first three-dimensional MRI image was generated using a first type of MRI sequence that is different from a second type of MRI sequence used to generate a second three-dimensional MRI image;

processing, for each three-dimensional MRI image of the plurality of three-dimensional MRI images, the three-dimensional MRI image using one or more corresponding encoder arms of a machine-learning model to generate an encoding of the three-dimensional MRI image, wherein the one or more corresponding encoder arms comprise a plurality of encoder models, wherein the plurality of encoder models comprises a first encoder model trained for the first type of MRI sequence and a second encoder model trained for the second type of MRI sequence, and wherein the first three-dimensional MRI image is processed by the first encoder model and the second three-dimensional MRI image is processed by the second encoder model;

concatenating the encodings of the plurality of three-dimensional MRI images to generate a concatenated representation; and processing the concatenated representation using a decoder arm of the machine-learning model to generate a prediction that identifies one or more portions of the volume of the brain predicted to depict at least part of a lesion.

15. The system of claim 14, wherein the set of actions further includes:

generating, for each three-dimensional MRI image of the plurality of three-dimensional MRI images, a downsampled encoding having a resolution that is lower than a resolution of the encoding of the three-dimensional MRI image;

processing, for each three-dimensional MRI image of the plurality of three-dimensional MRI images, the downsampled encoding using one or more layers of the one or more corresponding encoder arms; and concatenating the downsampled encodings to generate another concatenated representation, wherein the prediction is further based on processing of the another concatenated representation using the decoder arm of the machine-learning model.

16. The system of claim 14, wherein the machine-learning model includes one or more skip attention modules, each of the one or more skip attention modules connecting an encoding block of the one or more corresponding encoder arms of the machine-learning model to a decoder block of the decoder arm at a same resolution.

17. A computer-program product tangibly embodied in a non-transitory machine-readable storage medium, including instructions configured to cause one or more data processors to perform a set of actions including:

accessing a plurality of three-dimensional magnetic resonance imaging (MRI) images, wherein each of the plurality of three-dimensional MRI images depicts a same volume of a brain of a subject; and a first three-dimensional MRI image was generated using a first type of MRI sequence that is different from a second type of MRI sequence used to generate a second three-dimensional MRI image;

processing, for each three-dimensional MRI image of the plurality of three-dimensional MRI images, the three-dimensional MRI image using one or more corresponding encoder arms of a machine-learning model to generate an encoding of the three-dimensional MRI image, wherein the one or more corresponding encoder arms comprise a plurality of encoder models, wherein the plurality of encoder models comprises a first encoder model trained for the first type of MRI sequence and a second encoder model trained for the second type of MRI sequence, and wherein the first three-dimensional MRI image is processed by the first encoder model and the second three-dimensional MRI image is processed by the second encoder model;

concatenating the encodings of the plurality of three-dimensional MRI images to generate a concatenated representation; and processing the concatenated representation using a decoder arm of the machine-learning model to generate a prediction that identifies one or more portions of the volume of the brain predicted to depict at least part of a lesion.

18. The computer-implemented method of claim 1, wherein the first encoder model is trained using MRI images of the first type of MRI sequence, wherein the MRI images of the first type were preprocessed by performing normalization and/or resizing prior to training the first encoder model, and wherein the second encoder model is trained using MRI images of the second type of MRI sequence, wherein the MRI images of the second type are preprocessed by performing intensity rescaling and z-scoring prior to training the second encoder model.

19. The computer-implemented method of claim 2, wherein the first encoder model is trained to learn feature representations unique to the first type of MRI sequence, and the second encoder model is trained to learn feature representations unique to the second type of MRI sequence.

20. The computer-implemented method of claim 19, wherein the machine-learning model is trained by minimizing a loss function to simultaneously optimize weights of the plurality of encoder models.

* * * * *